United States Patent [19]
Sone et al.

[11] Patent Number: 6,048,523
[45] Date of Patent: Apr. 11, 2000

[54] POLYESTER CYCLIC COMPOUNDS, THEIR COMPLEXES AND BONDED BODIES

[75] Inventors: Hisao Sone, Fukuoka; Masaki Sakairi, Shinagawa-ku; Noriko Yoshizawa, Tsurugashima; Etsuko Isa, Niiza, all of Japan

[73] Assignee: Global Art Co. Ltd., Japan

[21] Appl. No.: 09/125,139

[22] PCT Filed: Feb. 10, 1997

[86] PCT No.: PCT/JP97/00353

§ 371 Date: Aug. 20, 1998

§ 102(e) Date: Aug. 20, 1998

[87] PCT Pub. No.: WO97/30042

PCT Pub. Date: Aug. 21, 1997

[30] Foreign Application Priority Data

Feb. 13, 1996 [JP] Japan ................................. P08-25615

[51] Int. Cl.[7] ........................ A61K 31/765; C08G 63/06
[52] U.S. Cl. ........................... 424/78.3; 528/361; 424/55; 424/78.08; 424/78.38; 424/486; 424/497
[58] Field of Search ............................. 528/361; 424/486, 424/497, 55, 78.08, 78.3, 78.38

[56] References Cited

FOREIGN PATENT DOCUMENTS 0 522 422  1/1993  European Pat. Off. .

OTHER PUBLICATIONS

Chemical Abstracts, vol. 89, No. 13, 1978, Columbus, Ohio, US; abstract No. 108036t, Dale et al, "Cyclic Oligoesters of Glycolic Acid", p. 790.
ACTA Chem. Scand. Ser. B, vol. B32, No. 4, 1978, Sweden, p. 306–307.

*Primary Examiner*—Samuel A. Acquah
*Attorney, Agent, or Firm*—Nixon & Vanderhye

[57] ABSTRACT

It is provided a polyester cyclic compound represented by formula (1). It is also provided a complex of a polyester cyclic compound represented by formula (1), (3) or (4) and a compound containing an OH group(s). It is still further provided a bonded body of an ester compound and the cyclic compound represented by the formula (1), (3) or (4), or the complex. The above-described compounds demonstrate various pharmacological effects, such as carcinostatic effect and immunological regulation, specifically to a living body. (In the formulae, each "R" is independently H, a $C_1$–$C_5$ alkyl group, or a $C_1$–$C_5$ alkyl group wherein one or more H is replaced by F, and "n" is an integer of 2 to 9).

18 Claims, No Drawings

POLYESTER CYCLIC COMPOUNDS, THEIR COMPLEXES AND BONDED BODIES

TECHNICAL FIELD

The present invention relates to a polyester cyclic compound, a complex of the cyclic compound and a compound containing a OH group or groups, and a bonded body of an ester compound and the cyclic compound or the complex, which demonstrate various pharmacological effects, such as carcinostatic effect and immunological regulation, to a living body.

BACKGROUND ART

Recently, relationship between enteric bacteria and carcinogenesis has been researched progressively. Particularly, it is said that change in intestinal bacterial flora plays a major role in the formation of carcinogens and substances for promoting carcinogenesis and their activation or suppression.

Especially, utility of lactic acid bacteria attracts attention and it is said that immune response of a host may be improved by supplying lactic acid bacteria or products of cultivation thereof, and that lactic acid bacteria may suppress proliferation of intestinal bacteria relating to production of carcinogens and carcinogenesis-promoting substances to suppress occurrence of tumors.

However, which substance among products of lactic acid bacteria provides such effects has not known yet.

Besides, Lactic acid is well known as a main substance produced by lactic acid bacteria. Lactic acid is an usual component in animal's bodies and is produced in muscles. Most of produced lactic acid is utilized as a substrate for TCA cycle or gluconeogenesis in the liver or kidney.

DISCLOSURE OF INVENTION

The inventors considered such circumstance and made intensive research on the subject, and finally found that specific polyester cyclic compound synthesized from a hydroxy acid such as lactic acid demonstrated various pharmacological effects, such as carcinostatic effect and immunological regulation, specifically to a living body.

The inventors further made research for improving the effects of the polyester cyclic compound and found that a complex formed by mixing and heating the polyester cyclic compound and a compound containing a OH group or groups (referred as "OH group-containing compound" below) demonstrated various pharmacological effects more specifically to a living body.

Moreover, the inventors found that the polyester cyclic compound or the complex bonded with an ester compound, such as a phosphoric ester, sulfuric ester or carbonic ester with a low or high molecular weight, to form a bonded body and be further stabilized. The bonded body also demonstrated various pharmacological effects.

The invention was established based on these discoveries. Namely, it is an object of the invention to provide a novel polyester cyclic compound, its complex and a bonded body of the polyester cyclic compound which demonstrate various pharmacological effects such as carcinostatic effect and immunological regulation.

To give a solution to the above problems, the invention provides a polyester cyclic compound represented by the following formula (1)

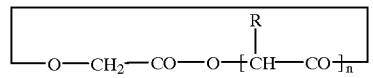

(1)

(in the formula (1), each "R" is independently hydrogen atom, an alkyl group having 1–5 carbon atoms, or an alkyl group having 1–5 carbon atoms wherein one or more hydrogen atom is replaced by a fluorine atom, and "n" is an integer of 2 to 9), or the following formula (2).

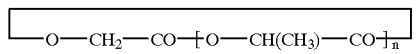

(2)

("n" is same as above).

The invention further provides a complex of at least one compound containing a OH group or groups therein and at least one polyester cyclic compound selected from a group consisting of a compound of the following formula (1), a compound of the following formula (3) and a compound of the following formula (4).

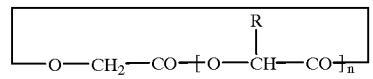

(1)

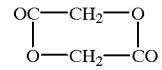

(3)

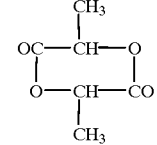

(4)

(in the formulas, "R" and "n" are same as above).

The invention further provides a bonded body obtained by bonding of at least one ester compound and at least one polyester cyclic compound selected from a group consisting of a compound of the following formula (1), a compound of the following formula (3) and a compound of the following formula (4)

(1)

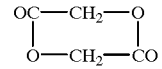

(3)

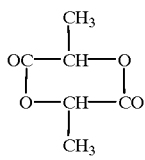

(in the formulas, "R" and "n" are same as above), or by bonding of at least one ester compound and at least one complex of said polyester cyclic compound and a compound containing a OH group or groups therein.

The polyester cyclic compound, complex of the polyester cyclic compound and bonded body demonstrate pharmacological effects, such as carcinostatic effect and immunological regulation specifically to a living body and hardly demonstrate any toxicity. Particularly, the complex demonstrates various pharmacological effects more specifically than the polyester cyclic compound. Moreover, the bonded body, obtained by bonding the polyester cyclic compound or the complex and an ester compound with a low or high molecular weight, also demonstrates various pharmacological effects as described above.

The reason why the pharmacological effects was improved by converting the polyester cyclic compound to the complex may be assumed as follows.

Namely, the complex is obtained from the polyester cyclic compound of the formula (1), (3), or (4) and an OH group-containing compound such as an alcohol, phenol or hydroxy acid compound. Such complex may be readily dissolved into water by the effect of the OH group-containing compound. Therefore, it is assumed that the polyester cyclic compound demonstrating various pharmacological effects is readily absorbed into a living body and further stabilized to improve its effects.

Moreover, the effect of the bonded body of an ester compound and the polyester cyclic compound or its complex may be assumed as follows.

Namely, it is assumed that the bonded body is obtained by the bonding, for example electrostatic bonding of the cyclic compound or its complex with a phosphoric group, sulfuric group or carbonic group of a phosphoric ester, sulfuric ester or carbonic ester with a low or high molecular weight. It is also assumed that the bonded body is stabilized in water by the effect of the thus bonded ester compound to improve the above pharmacological effects.

By the complex or the bonded body of the invention, the polyester cyclic compound may be utilized more effectively. Besides, such complex or bonded body may be applied for utilizing the OH group-containing compound more effectively. That is, when pharmacological effects or the other effects of the OH group-containing compound are to be expected, such OH group-containing compound may be reacted with one of various polyester cyclic compounds to provide a complex, or the complex may be bonded with the ester compound. As a result, the OH group-containing compound may be stabilized during preparing pharmacological compositions, in digestive tracts, and on skin or the like, the absorption effeciency of the OH group-containing compound may be improved in digestive tracts or from skin, and the complex or the bonded body may form micelles with a uniform diameter to promote the effeciency of drug delivery in a living body.

A medical or pharmaceutical composition containing, as its effective component, at least one of the polyester cyclic compound, or at least one complex of the polyester cyclic compound and an OH group-containing compound, or at least one bonded body obtained by bonding of an ester compound and the polyester cyclic compound or the complex may be applied to medication or prevention of cancer, rheumatism, prostic disease, dementia, chronic hepatitis, autoimmune disease, allergic diseases, menopausal syndrome, menstrual pain or adult diseases such as diabetes and hypertension.

BEST MODE FOR CARRYING OUT THE INVENTION

The preferred embodiments of the invention will be described below in detail.

First, the polyester cyclic compound of the formula (1) will be described. In the cyclic compound of the formula (1), repeating units in the formula may be same or different to each other. Number of carbon atoms of "R" may preferably be 1 to 3. The polyester cyclic compound may be obtained by subjecting one compound or mixture of two or more compounds, selected from a group consisting of hydroxy acids (oxyacids) of the following formula (5), to dehydration and polycondensation under heating condition to produce distillate fraction, and purifying it.

(in the formula, "R" is same as above. Number of carbon atoms of "R" is preferably 1 to 3).

The hydroxy acid as a starting material includes, for example, lactic acid, fluorolactic acid, glycollic acid or the like. Besides, a concentration of the hydroxy acid in raw material may preferably be higher to improve operation effeciency.

A temperature for heating the hydroxy acid is normally 100–250° C. and preferably be 100–200° C. When the temperature is lower than 100° C., the dehydration and polycondensation may not take place sufficiently. On the contrary, when the temperature is higher than 250° C., polycondensation may be overwhelmed by depolymerization, and dimers of the hydroxy acids may occasonary be formed.

Final pressure during the dehydration and polycondensation is normally 30–1 mmHg and preferably 10–1 mmHg. When the pressure is higher than 30 mmHg, the dehydration and polycondensation may not take place sufficiently. On the contrary, the pressure set below 1 mmHg does not provide further effects and rather results in poor efficiency.

A time period for the dehydration and polycondensation is normally not less than 2 hours and preferably 4–10 hours.

The polyester cyclic compound of the formula (1) includes, for example, compounds of the above formula (2). The polyester cyclic compound of the formula (2) may be obtained by subjecting lactic acid to dehydration and polycondensation under heating condition to produce distillate fraction and purifying it. When synthesizing the compound of the formula (2), practical operations may be carried out, for example, according to the following procedure.

First, lactic acid as a starting material is prepared. Lactic acid may be selected voluntarily from L-, D- and DL-lactic acids, which may be used alone or in combination. Besides, in the viewpoint of operation effeciency, a concentration of lactic acid may preferably be higher.

Lactic acid is then reacted to remove water in a condition of a temperature of not lower than 100° C. and a pressure of 760 mmHg–300 mmHg for not less than 2 hours. For example, Lactic acid is reacted for 4 to 6 hours in reduced pressures while gradually increasing reaction temperatures from 100° C. to 140° C. and reducing pressures from 760 mmHg to 300 mmHg.

Thereafter, lactic acid is subjected to polycondensation to recover distillate fraction, at a temperature of not lower than 100° C. and a pressure of 10 mmHg–1 mmHg for not less than 2 hours, for example, at 140° C./10 mmHg for 4–6 hours.

After the reaction is completed, the above distillate fraction is purified.

The purification is accomplished by dissolving the distillate fraction into an organic solvent, which has the ability to dissolve the crystals of the distillate, such as ethyl acetate or chloroform, and by then carrying out partition extraction using an alkali solution such as sodium hydroxide solution and sodium bicarbonate solution.

After the purification, recrystallization using an organic solvent such as diethylether results in the compound of the formula (2).

The compound may be synthesized only from lactic acid without any catalysts and is a polyester cyclic compound comprising an ester bonding of n moles of lactic acid and one mole of demethylized lactic acid.

The compound of the formula (2) specifically includes the compounds having the following structures (6) and (7).

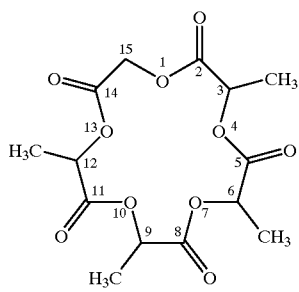

(6)

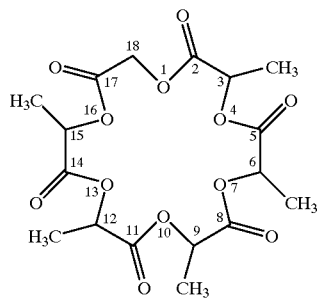

(7)

The polyester cyclic compound demonstrates various pharmacological effects such as carcinostatic effect and immunological regulation specifically to a living body and hardly demonstrates any toxicity. Therefore, the compound is particularly effective for medication or prevention of cancer, rheumatism, prostic disease, dementia, chronic hepatitis, autoimmune disease, allergic diseases, menopausal syndrome, menstrual pain or adult diseases such as diabetes and hypertension.

The complex of the polyester cyclic compound provided by the invention will be explained below. The complex of the invention is composed of the OH group-containing compound and the polyester cyclic compound of the formula (1), (3) or (4). Such complex may be obtained, for example, by mixing and heating the OH group-containing compound and the polyester cyclic compound. The complex may be obtained by mixing one or more polyester cyclic compound and one or more OH group-containing compound.

The polyester cyclic compound, as a starting material for the complex, not only includes the compound of the formula (1) and but also includes the compounds of the formulas (3) and (4). The compound of the formula (3) is a glycollide and the compound of the formula (4) is a lactide. These two compounds are known. The polyester cyclic compound may be used alone, or two or more compounds may be used in combination. Moreover, commercial glycollide or lactide may be used and, when the glycollide or lactide includes optical isomers, each of the isomers may be used.

The OH group-containing compound as the other starting material of the complex includes generally an organic compound or an inorganic compound each containing an OH group. However, an organic compound having an alcoholic hydroxyl group or a phenolic hydroxyl group, or an hydroxy acid may be normally used. The organic compound containing an OH group includes, for example, monovalent or polyvalent alcohols (including primary, secondary and tertially alcohols) such as methanol, ethanol, 2-butanol, propylene glycol, saccharides; monovalent or polyvalent phenols such as phenol, cresol, catecol; hydroxy acids such as glycollic acid, lactic acid, tartaric acid. The OH group-containing compound may be a mixture of two or more compounds selected from the above listed compounds and their salts.

The OH group-containing compound may be newly synthesized, or commercially available. When the compound includes optical isomers, each isomer may be used. When the OH group-containing compound is of crystalline form, the crystal may preferably dissolved into a solvent, which readily dissolves the crystal and does not react with the polyester cyclic compound, such as dimethylsulfoxide, to provide solution which is used for the reaction with the cyclic compound.

The polyester cyclic compound and the OH group-containing compound are prepared, then charged into a reaction container, and heated for a predetermined time period. A temperature for the heating is not less than a room temperature and preferably 50–100° C.

A time period for the reaction may be properly determined depending on the properties of the OH group-containing compound and the heating temperature. Generally, the higher the heating temperature, the shorter the reaction time period, and the lower the heating temperature, the longer the reaction time period.

It is used a reaction container which does not reacts with the polyester cyclic compound and the OH group-containing compound and has a structure not leaking the evaporated OH group-containing compound during heating. For example, a closed glass container or a glass container with a reflux condenser may be used.

Thereafter, unreacted OH group-containing compound was removed by distillation under a reduced pressure or another method, and the thus obtained product was purified by means of a separating method such as partition extraction or chromatography to obtain the complex of the polyester cyclic compound of the invention.

The thus purified complex may be confirmed by retention times (referred to as "RT" below) of peaks, which is obtained by concentration gradient elution using water-acetonitrile by means of high performance liquid chromatography (referred to as "HPLC" below) with a detector of ultraviolet light and visible light using an ODS column.

Generally, a saturated alcohol or a saccharide does not provide a UV absorption peak at 210 nm, a phenol, a hydroxy acid and a salt of neutralized hydroxy acid provide UV peaks at characteristic RT's, respectively. However, the complex of the polyester cyclic compound provides a UV peak at an RT different from the RT's of the above compounds.

The thus obtained complex may be readily separated into the polyester cyclic compound and the OH group-containing compound by heating it with water for a long time. Therefore, the complex obtained by the above reaction is considered to be a so called "complex" formed by the polyester cyclic compound and the OH group-containing compound.

The thus obtained complex demonstrates various pharmacological effects such as carcinostatic effect and immunological regulation specific to a living body of human and animals. Moreover, the complex hardly demonstrates any toxicity. Therefore, the complex is particularly effective for medication or prevention of cancer, rheumatism, prostic disease, dementia, chronic hepatitis, autoimmune disease, allergic diseases, menopausal syndrome, menstrual pain or adult diseases such as diabetes and hypertension.

The complex forms micelles by the effect of the OH group-containing compound to be easily dissolved into water when mixed with water. The complex may be more readily bonded with an ester compound such as a phosphoric ester, a sulfuric ester or a carbonic ester each having a low or high molecular weight. Therefore, it is assumed that the polyester cyclic compound, demonstrating various pharmacological effects, may be easily absorbed into a living body and is more stabilized to improve the effects.

While, when the OH group-containing compound has 4 or more carbon atoms, its solubility to water is generally small. However, when such OH group-containing compound is reacted with the polyester cyclic compound represented by the formula (1) to (4) or the like to form the complex, it forms micelles in water to be readily dissolved into water. Moreover, the stability of the OH group-containing compound itself is improved.

Therefore, by forming the complex of the OH group-containing compound and the polyester cyclic compound, the OH group-containing compound may be stabilized during preparing pharmacological compositions, in digestive tracts, or on skin or the like, the absorption effeciency of the OH group-containing compound may be improved in digestive tracts or from skin, and the complex may form micelles with a uniform diameter to promote the effeciency of drug delivery in a living body.

The bonded body may be obtained by bonding the polyester cyclic compound or the complex and an ester compound such as a phosphoric ester, a sulfuric ester or a carbonic ester each having a low or high molecular weight. Particularly, the ester compound may form a bond more easily with the complex which may be readily dissolved into water. It was difficult to isolate the bonded body, however, its characteristic peak was confirmed by means of HPLC. Moreover, when the ester compound was removed from the bonded body by alkali-neutralization extraction and the thus obtained product was measured by HPLC again, the characteristic peak of the original polyester cyclic compound or the complex was confirmed. From such results, it is assumed that the bonded body is formed by the bonding, for example, electrostatic bonding of the polyester cyclic compound or its complex with a phosphoric group, sulfuric group or carbonic group of the ester compound. By the effect of the thus bonded ester compound, it is assumed that the bonded body becomes more stable in water and therefore the above pharmacological effects was further improved.

EXAMPLES

The present invention will be further explained below in detail referring to the following examples.

First, the polyester cyclic compounds of the formulas (1) to (4) are synthesized as shown in examples 1 to 8 and explained in detail.

Example 1

The Compound of Formula (1) Wherein "R" is $CH_3$: Same as the Compound of Formula (2)

200 ml of (L- or DL-) lactic acid was heated in nitrogen flow at 140° C./300 mmHg for 1 hour to remove distilled water. Lactic acid was then heated at temperatures which were gradually increased from 140° C. to 180° C. at 10 mmHg so that it was dehydrated and polycondensed for 4 hours to produce distillate.

The distillate was dissolved in ethyl acetate and subjected to partition extraction using saturated aqueous solution of sodium bicarbonate to obtain about 15 grams of crystal, which was then dissolved into diethyl ether and subjected to a recrystallization procedure. Consequently, non-colored transparent needle-shaped crystal was obtained when L-lactic acid was used, and plated-shaped crystal was obtained when DL-lactic acid was used.

The thus obtained crystal was developed on a silica-gel thin layer chromatography (TLC) using a developing solvent of benzene:ethyl acetate=76:24. Spots were shown on positions of Rf's of 0.7 to 0.8.

The acid value and ester value of the crystal were also measured as 0 and 760 to 830, respectively.

Moreover, the nuclear magnetic resonance (NMR) spectrum of the crystal was analyzed, so that methylene group was confirmed.

Moreover, the crystal was subjected to gas-mass spectrum analysis to measure molecular weights of compounds contained in the crystal. The spectrum showed peaks confirming the presence of the compounds of the formula (1) wherein "R" was $CH_3$ and "n"=2–9.

Example 2

The Compound of Formula (1) Wherein "R" is $CH_3$: Same as the Compound of Formula (2)

200 ml of L-lactic acid was charged into a four-necked flask (reaction container) equipped with a thermometer, a condenser and a nitrogen inducing tube and heated in nitrogen flow at 140° C./300 mmHg for 1 hour so that it was dehydrated. Thereafter, distilled water in the condenser was removed. The content in the container was then reacted at 140° C./10 mmHg for 1 hour and subsequently at 180° C./10 mmHg for 3 hours to obtain about 50 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 10 grams of non-colored transparent needle-shaped crystal.

Example 3

The Compound of Formula (1) Wherein "R" is $CH_3$: Same as the Compound of Formula (2)

100 ml of L-lactic acid was charged into the reaction container same as Example 2 and heated in nitrogen flow at 140° C./300 mmHg for 1 hour so that it was dehydrated.

Distilled water in the condenser was then removed. The content in the container was further reacted at 140° C./10 mmHg for 4 hours and subsequently at 180° C./10 mmHg for 6 hours to obtain about 24 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 10 grams of non-colored transparent needle-shaped crystal.

Example 4

The Compound of Formula (1) Wherein "R" is $CH_3$: Same as the Compound of Formula (2)

150 ml of L-lactic acid was charged into the reaction container same as Example 2 and heated in nitrogen flow at 140° C. for 2 hours gradually reducing the pressure from 760 mmHg to 30 mmHg, so that it was dehydrated. Distilled water in the condenser was then removed. The content in the container was further reacted at 140° C./10 mmHg for 3 hours to obtain about 23 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 10 grams of non-colored transparent needle-shaped crystal.

Example 5

The Compound of Formula (1) Wherein "R" is an Alkyl Group Having 2 Carbon Atoms 100 ml of 2-hydroxy butyric acid was charged into the reaction container same as Example 2 and heated in nitrogen flow at 140° C. for 2 hours gradually reducing the pressure from 760 mmHg to 30 mmHg, so that it was dehydrated. Distilled water in the condenser was then removed. The content of the container was further reacted at 180° C./10 mmHg for 3 hours to obtain about 13 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 7 grams of non-colored transparent needle-shaped crystal.

Example 6

The Compound of Formula (1) Wherein "R" is $CF_3$ 100 ml of trifluoro lactic acid was charged into the reaction container same as Example 2 and heated in nitrogen flow at 140° C. for 2 hours gradually reducing the pressure from 760 mmHg to 10 mmHg, so that it was dehydrated. Distilled water in the condenser was then removed. The content of the container was further reacted at 180° C./10 mmHg for 3 hours to obtain about 16 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 9 grams of non-colored transparent needle-shaped crystal.

Example 7

The Compound of Formula (3)

100 grams of glycollic acid was charged into the reaction container same as Example 2 and heated in nitrogen flow at 140° C. for 5 hours gradually reducing the pressure from 760 mmHg to 10 mmHg, so that it was reacted to obtain about 20 grams of distillate in the condenser.

The distillate was dissolved in an appropriate amount of ethyl acetate and subjected to partition extraction using saturated aqueous solution of sodium bicarbonate.

The thus obtained purified substance was dissolved into acetone and recrystallized to obtain about 12 grams of non-colored transparent plate-shaped crystal.

Example 8

The Compound of Formula (4)

100 ml of L-lactic acid was charged into the reaction container same as Example 2 and heated in nitrogen flow at 180–220° C./25 mmHg for 5 hours, so that it was dehydrated and polycondensed to obtain about 28 grams of distillate in the condenser.

The distillate was dissolved in an appropriate amount of ethyl acetate and subjected to partition extraction using saturated aqueous solution of sodium bicarbonate.

The thus obtained purified substance was dissolved into diethyl ether and recrystallized to obtain about 15 grams of pale-yellow transparent needle-shaped crystal.

Then, polyester cyclic compound complexes, which is obtained from the OH group-containing compound and the polyester cyclic compounds of the formula (1) to (4), will be exemplified in the following examples 9 to 32 and explained in detail.

Example 9

1 gram of the polyester cyclic compound obtained in Example 4 and 1 ml of methanol were charged in an air-tight container with "Teflon" packing or a glass container with a condenser, and heated at 100° C. for more than 12 hours to obtain reaction solution containing a complex of the polyester cyclic compound and methanol.

The reaction solution was distilled under a reduced pressure to remove unreacted methanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 10

1 gram of the polyester cyclic compound obtained in Example 4 and 1 ml of ethanol were charged in an air-tight container with "Teflon" packing or a glass container with a condenser, and heated at 100° C. for more than 12 hours to obtain reaction solution containing a complex of the polyester cyclic compound and ethanol.

The reaction solution was distilled under a reduced pressure to remove unreacted ethanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 11

1 gram of the polyester cyclic compound obtained in Example 4 and 1 ml of propanol were charged in an air-tight container with "Teflon" packing or a glass container with a condenser, and heated at 100° C. for more than 12 hours to obtain reaction solution containing a complex of the polyester cyclic compound and propanol.

The reaction solution was distilled under a reduced pressure to remove unreacted propanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 12

1 gram of the polyester cyclic compound obtained in Example 4 and 1 ml of butanol were charged in an air-tight container with "Teflon" packing or a glass container with a condenser, and heated at 100° C. for more than 12 hours to obtain reaction solution containing a complex of the polyester cyclic compound and butanol.

The reaction solution was distilled under a reduced pressure to remove unreacted butanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 13

1 gram of the polyester cyclic compound obtained in Example 4 and 1 ml of pentanol were charged in an air-tight container with "Teflon" packing or a glass container with a condenser, and heated at 100° C. for more than 12 hours to obtain reaction solution containing a complex of the polyester cyclic compound and pentanol.

The reaction solution was distilled under a reduced pressure to remove unreacted pentanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 14

1 gram of the polyester cyclic compound obtained in Example 4 and 1 ml of hexanol were charged in an air-tight container with "Teflon" packing or a glass container with a condenser, and heated at 100° C. for more than 12 hours to obtain reaction solution containing a complex of the polyester cyclic compound and hexanol.

The reaction solution was distilled under a reduced pressure to remove unreacted hexanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 15

1 gram of the polyester cyclic compound obtained in Example 4 and 1 ml of heptanol were charged in an air-tight container with "Teflon" packing or a glass container with a condenser, and heated at 100° C. for more than 12 hours to obtain reaction solution containing a complex of the polyester cyclic compound and heptanol.

The reaction solution was distilled under a reduced pressure to remove unreacted heptanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 16

1 gram of the polyester cyclic compound obtained in Example 4 and 1 ml of octanol were charged in an air-tight container with "Teflon" packing or a glass container with a condenser, and heated at 100° C. for more than 12 hours to obtain reaction solution containing a complex of the polyester cyclic compound and octanol.

The reaction solution was distilled under a reduced pressure to remove unreacted octanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 17

1 gram of the polyester cyclic compound obtained in Example 4 and 1 ml of nonanol were charged in an air-tight container with "Teflon" packing or a glass container with a condenser, and heated at 100° C. for more than 12 hours to obtain reaction solution containing a complex of the polyester cyclic compound and nonanol.

The reaction solution was distilled under a reduced pressure to remove unreacted nonanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 18

1 gram of the polyester cyclic compound obtained in Example 4 and 1 ml of decanol were charged in an air-tight container with "Teflon" packing or a glass container with a condenser, and heated at 100° C. for more than 12 hours to obtain reaction solution containing a complex of the polyester cyclic compound and decanol.

The reaction solution was distilled under a reduced pressure to remove unreacted decanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 19

1 gram of the polyester cyclic compound obtained in Example 4 and 1 ml of undecanol were charged in an air-tight container with "Teflon" packing or a glass container with a condenser, and heated at 100° C. for more than 12 hours to obtain reaction solution containing a complex of the polyester cyclic compound and undecanol.

The reaction solution was distilled under a reduced pressure to remove unreacted undecanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 20

1 gram of the polyester cyclic compound obtained in Example 4 and 1 ml of dodecanol were charged in an air-tight container with "Teflon" packing or a glass container with a condenser, and heated at 100+ C. for more than 12 hours to obtain reaction solution containing a complex of the polyester cyclic compound and dodecanol.

The reaction solution was distilled under a reduced pressure to remove unreacted dodecanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 21

1 gram of the polyester cyclic compound obtained in Example 4 and 1 ml of 2-butanol were charged in an air-tight container with "Teflon" packing or a glass container with a condenser, and heated at 100° C. for more than 12 hours to obtain reaction solution containing a complex of the polyester cyclic compound and 2-butanol.

The reaction solution was distilled under a reduced pressure to remove unreacted 2-butanol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 22

1 gram of the polyester cyclic compound obtained in Example 4 and 1 ml of phenol were charged in an air-tight container with "Teflon" packing or a glass container with a condenser, and heated at 100° C. for more than 12 hours to obtain reaction solution containing a complex of the polyester cyclic compound and phenol.

The reaction solution was distilled under a reduced pressure to remove unreacted phenol and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 23

1 gram of the polyester cyclic compound obtained in Example 4 and 1 ml of propylene glycol were charged in an air-tight container with "Teflon" packing or a glass container with a condenser, and heated at 100° C. for more than 12 hours to obtain reaction solution containing a complex of the polyester cyclic compound and propylene glycol.

The reaction solution was purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 24

1 gram of the polyester cyclic compound obtained in Example 4 and 1 ml of glycerin were charged in an air-tight container with "Teflon" packing or a glass container with a condenser, and heated at 100° C. for more than 12 hours to obtain reaction solution containing a complex of the polyester cyclic compound and glycerin.

The reaction solution was purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed in each experiment.

Example 25

1 gram of the polyester cyclic compound obtained in Example 4 and 1 ml of lactic acid were charged in an air-tight container with "Teflon" packing or a glass container with a condenser, and heated at 100° C. for more than 12 hours to obtain reaction solution containing a complex of the polyester cyclic compound and lactic acid.

The reaction solution was purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 26

1 gram of the polyester cyclic compound obtained in Example 4, 1 gram of calcium lactate and 10 ml of dimethyl sulfoxide were charged in an air-tight container with "Teflon" packing or a glass container with a condenser, and heated at 100° C. for more than 12 hours to obtain reaction solution containing a complex of the polyester cyclic compound and calcium lactate.

The reaction solution was distilled under a reduced pressure to remove dimethyl sulfoxide and purified by means of an open column chromatography filled with ODS to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 27

1 gram of the polyester cyclic compound obtained in Example 4 and 1 gram of sodium 4-hydroxybutyrate were charged in an air-tight container with "Teflon" packing or a glass container with a condenser, and heated at 100° C. for more than 12 hours to obtain reaction product containing a complex of the polyester cyclic compound and sodium 4-hydroxybutyrate.

The reaction product was dissolved in water and extracted with ethyl acetate to obtain about 1 ml of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 ml of the complex was obtained and its characteristic peak, which was not shown in the starting compounds, was confirmed by HPLC in each experiment.

Example 28

1 gram of the polyester cyclic compound obtained in Example 4 and 1 gram of 12-hydroxydodecanoic acid were charged in an air-tight container with "Teflon" packing or a glass container with a condenser, and heated at 100° C. for more than 12 hours to obtain reaction product containing a complex of the polyester cyclic compound and 12-hydroxydodecanoic acid.

The reaction product was extracted with ethyl acetate to obtain about 1 g of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 g of the complex was obtained and its characteristic peak, which was not shown in the starting compounds, was confirmed by HPLC in each experiment.

Example 29

1 gram of the polyester cyclic compound obtained in Example 4 and 1 gram of 16-hydroxyheptadecanoic acid were charged in an air-tight container with "Teflon" packing or a glass container with a condenser, and heated at 100° C. for more than 12 hours to obtain reaction product containing a complex of the polyester cyclic compound and 16-hydroxyheptadecanoic acid.

The reaction product was extracted with ethyl acetate to obtain about 1 g of the complex. By means of HPLC, the thus obtained complex was confirmed by its characteristic peak not shown in the starting compounds.

Moreover, the above experiment was carried out using each polyester cyclic compound obtained in each of Examples 5 to 8. Consequently, about 1 g of the complex was obtained and its characteristic peak, which was not shown in the starting compounds, was confirmed by HPLC in each experiment.

Various properties, such as stability, of the polyester cyclic compound, the complex of the polyester cyclic compound and the bonded body of the polyester cyclic compound and the ester compound, will be explained below in detail referring to examples 30 to 32.

Example 30

10 mg of the polyester cyclic compound of the formula (2), and the complex obtained from the compound of the formula (2) and ethanol, butanol or hexanol were charged respectively and 1 ml of distilled water was added. The thus obtained mixture was allowed to stand for 24 hours and then subjected to HPLC for evaluating the stability in water.

The polyester cyclic compound of the formula (2) was hydrolyzed 97% after 24 hours and its characteristic peak was almost disappeared. However, each characteristic peak of the complex of the compound of the formula (2) and ethanol, butanol or hexanol was not disappeared and could be 100% confirmed after 24 hours, 72 hours, 7 days and 14 days.

As seen from this experimental results, the complex obtained from the polyester cyclic compound and the OH group-containing compound is more stable than the polyester cyclic compound itself.

Example 31

The polyester cyclic compound of the formula (2), and the complex obtained from the compound of the formula (2) and ethanol, butanol or hexanol were dissolved into 100 mM phosphate buffer solution (pH=6.8) respectively and then subjected to HPLC. Consequently, the characteristic peaks of the cyclic compound and the complexes were disappeared and new different peaks were appeared near column void. When each of the thus obtained solutions was extracted with ethyl acetate and the resultant extract was subjected to HPLC again. Consequently, each characteristic peak of the cyclic compound or its complex was confirmed.

As seen from this results, the polyester cyclic compound and their complexes form bonded compounds with phosphoric acid in solution of phosphoric acid.

Example 32

10 mg of the polyester cyclic compound of the formula (2), and the complex obtained from the compound of the formula (2) and butanol or hexanol were added to 1 ml of 10% aqueous solution of casein or carrageenan and stirred, so that agglomeration was observed.

Casein is one of proteins and has a phosphoric ester group. Carrageenan is one of polysaccharides and has a sulfuric ester group. Therefore, it is assumed that the polyester cyclic compound of the formula (2) or its complex forms a bonded body with the phosphoric acid group or the sulfuric acid group and agglomerates.

In vitro experimental results will be shown below in examples 33 and 34 and explained in detail, using the polyester cyclic compound of the formula (2) or (4), or the complex of the cyclic compound of the formula (2) or (4) and the OH group-containing compound.

Example 33

To a multi-plate having 24 holes seeded with Yoshida sarcoma cells in a concentration of $1 \times 10^4$ per one hole, culture solution was charged containing the cyclic compound of the formula (2) or (4), or the complex obtained from the compound of the formula (2) or (4) and butanol or hexanol. A concentration of each compound or complex in the culture solution was adjusted to 1 mg/ml, 0.5 mg/ml, 0.25 mg/ml or 0.125 mg/ml. After the sarcoma cells were cultivated for 3 days, the number of the cells was measured. The suppression rates (%) of the compounds and complexes to control were shown in the following table.

TABLE 1

| Compound | suppression rate to control (%) | | | |
|---|---|---|---|---|
| | 1 mg | 0.5 mg | 0.25 mg | 0.125 mg |
| formula (2) | 44.5 | 2.3 | 0 | 0 |
| formula (4) | 40.9 | 0 | 0 | −18.2 |
| complex of formula (2) and butanol | 74.3 | 57.5 | 28.3 | 8.8 |
| complex of formula (4) and butanol | 75.2 | 54.7 | 19.5 | 1.8 |
| complex of formula (2) and hexanol | 100 | 71.6 | 33.3 | 18.5 |

TABLE 1-continued

| Compound | suppression rate to control (%) | | | |
|---|---|---|---|---|
| | 1 mg | 0.5 mg | 0.25 mg | 0.125 mg |
| complex of formula (4) and hexanol | 100 | 67.9 | 23.5 | 17.3 |

As seen from the above results, all the compounds of the formula (2) and (4), and the complexes obtained from the compounds reacted with butanol or hexanol suppressed the proliferation of Yoshida sarcoma cells. The suppression effect of the complexes was higher than that of the polyester cyclic compounds.

Example 34

To an MRS medium, the polyester cyclic compound of the formula (2) or (4), or the complex obtained from the compound of the formula (2) or (4) and butanol, hexanol, octanol or decanol was dissolved in a concentration of 0.25 mg/10 ml. Pre-cultivated lactic acid bacteria were seeded into each MRS medium in a predetermined amount. After 48 hours, it was diluted to a predetermined magnification and inoculated on an MRS agar medium to measure the number of the bacteria. The multiplication rates (%) to control were shown in the following table.

TABLE 2

| Compound | Multiplication rates (%) |
|---|---|
| control | 0 |
| formula (2) | 15.7 |
| complex of formula (2) and butanol | 105.3 |
| complex of formula (2) and hexanol | 31.6 |
| complex of formula (2) and octanol | 31.6 |
| complex of formula (2) and decanol | 21.1 |
| formula (4) | 115.8 |
| complex of formula (4) and butanol | 15.8 |
| complex of formula (4) and hexanol | 415.8 |
| complex of formula (4) and decanol | 31.6 |

As seen from the results, all the compounds of the formula (2) and (4), and their complexes with the OH group-containing compounds improved the multiplication rates of lactic acid bacteria. The multiplication rates of the complexes were generally higher than those of the polyester cyclic compounds, although the rates varies depending on which OH group-containing compound was reacted.

Biological test results will be shown below in Examples 35 to 42 and explained in detail, using the polyester cyclic compound of the formula (2) or (4), or the complex of the polyester cyclic compound of the formula (2) or (4) and the OH group-containing compound.

Example 35

Yoshida sarcomas were transplanted into a Donryu-rat of an age of 5 weeks. After stabilization of the sarcoma was confirmed, the cyclic compound of the formula (2) or (4), or the complex obtained from the compound of the formula (2) or (4) and butanol, hexanol, octanol or decanol was orally administered as a test sample for 2 weeks continually at a dose of 8 mg/kg/day. After the administration, sizes of the sarcomas were measured. The results were shown below.

TABLE 3

| Test group | Size of sarcoma (mm³) | Suppression rate (%) |
| --- | --- | --- |
| control | 7642.1 | 0 |
| formula (2) | 662.4 | 91.3 |
| complex of formula (2) and butanol | 583.0 | 92.4 |
| complex of formula (2) and hexanol | 2768.2 | 63.8 |
| complex of formula (2) and octanol | 2145.9 | 71.9 |
| complex of formula (2) and decanol | 2067.5 | 72.9 |
| formula (4) | 3216.6 | 57.9 |
| complex of formula (4) and butanol | 1023.7 | 86.6 |
| complex of formula (4) and hexanol | 3320.2 | 56.6 |
| complex of formula (4) and decanol | 3486.9 | 54.4 |

(All the values in the table were average values. Sizes of the sarcomas were indicated in mm³.)

As seen from the above results, all of the compounds of the formula (2) and (4), and their complexes with the OH group-containing compounds showed suppression effect on the proliferation of the sarcomas. The suppression effect of the complexes were varied depending on which OH group-containing compound was reacted with the polyester cyclic compound.

Example 36

Yoshida sarcomas were transplanted into a Donryu-rat of an age of 5 weeks. After stabilization of the sarcoma was confirmed, the cyclic compound of the formula (2), or the complex obtained from the compound of the formula (2) and butanol or hexanol was subcutaneously administered as a test sample for 2 weeks continually at a dose of 8 mg/kg/day. After the administration, sizes of the sarcomas were measured. The results were shown below.

TABLE 4

| Test group | Size of sarcoma (mm³) | Suppression rate (%) |
| --- | --- | --- |
| control | 9389.3 | 0 |
| formula (2) | 4320.0 | 54.0 |
| complex of formula (2) and butanol | 910.0 | 90.3 |
| complex of formula (2) and hexanol | 342.0 | 96.4 |

(All the values in the table were average values. Sizes of the sarcomas were indicated in mm³.)

As seen from the above results, all of the compound of the formula (2), and its complexes with the OH group-containing compounds showed suppression effect on the proliferation of the sarcomas. The suppression effect of the complexes was higher than that of the polyester cyclic compound. The suppression effect of the complexes was varied depending on which OH group-containing compound was reacted with the polyester cyclic compound.

Example 37

Yoshida sarcomas were transplanted into a Donryu-rat of an age of 5 weeks. After stabilization of the sarcoma was confirmed, the polyester cyclic compound of the formula (2), or the complex obtained from the compound of the formula (2) and butanol or hexanol was administered into the veins of the tail as a test sample for 10 days continually at a dose of 8 mg/kg/day. After the administration, sizes of the sarcomas were measured. The results were shown below.

TABLE 5

| Test group | Size of sarcoma (mm³) | Suppression rate (%) |
| --- | --- | --- |
| control | 5054.4 | 0 |
| formula (2) | 2960.5 | 41.4 |
| complex of formula (2) and butanol | 2386.8 | 52.8 |
| complex of formula (2) and hexanol | 324.0 | 93.6 |

(All the values in the table were average values. Sizes of the sarcomas were indicated in mm³.)

As seen from the above results, all of the polyester cyclic compound of the formula (2), and its complexes with the OH group-containing compounds showed suppression effect on the proliferation of the sarcomas. The suppression effect of the complexes was higher than that of the polyester cyclic compound. The suppression effect of the complexes was varied depending on which OH group-containing compound was reacted with the polyester cyclic compound.

Example 38

The polyester cyclic compound of the formula (2) or (4), or the complex obtained from the compound of the formula (2) or (4) and hexanol was charged in a test tube in an amount of 5 mg, 10 mg or 20 mg. 1 ml of whole blood of a rat was added into each test tube and the hemolytic effect of each compound or complex to the blood was observed. The results were shown below.

TABLE 6

| Compound/concentration | 5 mg | 10 mg | 20 mg |
| --- | --- | --- | --- |
| formula (2) | + | ++ | +++ |
| complex of formula (2) and hexanol | ++ | +++ | +++ |
| formula (4) | ± | ± | ± |
| complex of formula (4) and hexanol | ++ | +++ | +++ |

As seen from the above results, all of the polyester cyclic compounds of the formula (2) and (4), and the complexes obtained from the cyclic compounds and the OH group-containing compound showed hemolytic effect on blood.

Considering the above results and the results of Example 32, it is assumed that the cyclic compound or the complex specifically reacts with phosphoric acid groups of phospholipids on cell membranes of erythrocytes to affect the cell membranes and thereby results in hemolytic effect. In such point of view, it is considered that the complex obtained by reacting a drug having an OH group or groups with the polyester cyclic compound may provide a new drug readily absorbable to a living body and having superior phamacological action.

Example 39

The polyester cyclic compound of the formula (2) or (4), or the complex obtained from the compound of the formula (2) and butanol, hexanol or glycerin was orally administered to a SD rat as a test sample for 4 weeks at a dose of 4 mg/kg/day. After the administration, liquid paraffin was administered into peritoneal cavity of each rat. Three days later, peritoneal exudate cells were taken. Migration ability of macrophages produced from the peritoneal exudate cells was tested by glass capillary method. After 24 hours, a migration area of the macrophage was measured and a ratio of the measured migration area to that of control group was calculated. The results were shown below.

TABLE 7

| Test group | Ratio of the migration area |
| --- | --- |
| control | 1.00 |
| formula (2) | 1.73 |
| complex of formula (2) and butanol | 4.00 |
| complex of formula (2) and hexanol | 2.13 |
| complex of formula (2) and glycerin | 1.44 |
| formula (4) | 1.13 |

As seen from the results, all of the polyester cyclic compounds of the formula (2) and (4), and the complexes obtained from the cyclic compound and the OH group-containing compounds improved the migration ability of macrophages of the rats. The migration ability of macrophages was more improved by the complexes than by the polyester cyclic compounds. Moreover, the migration ability of the complex was varied depending on which OH group-containing compound was reacted with the cyclic compound.

Example 40

The polyester cyclic compound of the formula (2) or (4), or the complex obtained from the compound of the formula (2) and methanol, ethanol or butanol was orally administered to a rat as a test sample for 4 weeks at a dose of 4 mg/kg/day. After the administration, content of the bowel of each rat was taken, diluted to a predetermined magnification and inoculated on an MRS agar medium to measure the number of lactic acid bacteria in the bowel. The ratios of the measured numbers to that of the control were shown in the following table.

TABLE 8

| Test group | Ratio to control |
| --- | --- |
| control | 1 |
| formula (2) | 1 |
| complex of formula (2) and methanol | 6.6 |
| complex of formula (2) and ethanol | 12.8 |
| complex of formula (2) and butanol | >20 (★) |
| formula (4) | 3.8 |

(★) The ratio exceeded 20: upper limit of the measurement.

(★) The ratio exceeded 20:upper limit of the measurement.

As seen from the results, the polyester cyclic compound of the formula (4), and the complexes obtained from the cyclic compound of the formula (2) and the OH group-containing compounds improved the multiplication rate of lactic acid bacteria. The multiplication rates of lactic acid bacteria were more improved by the complexes than by the polyester cyclic compounds. Moreover, the multiplication rates of lactic acid bacteria were varied depending on which OH group-containing compound was reacted with the cyclic compound.

Example 41

The polyester cyclic compound of the formula (2), or the complex obtained from the compound of the formula (2) and butanol or hexanol was administered to a rat one time via oral or the tail vein in order to examine non effective dose. The cyclic compound of the formula (2) could not be administered into the tail vein and therefore was administered into peritoneal cavity. The results were shown below.

TABLE 9

| Administration route | Compound | Dose |
| --- | --- | --- |
| via oral | formula (2) | not less than 3000 mg/kg |
| | complex of formula (2) and butanol | not less than 3000 mg/kg |
| | complex of formula (2) and hexanol | not less than 3000 mg/kg |
| via tail vein | complex of formula (2) and butanol | not less than 300 mg/kg |
| | complex of formula (2) and hexanol | not less than 300 mg/kg |
| via peritoneal cavity | formula (2) | not less than 200 mg/kg |

Example 42

The cyclic compound of the formula (2) or (4), or the complex obtained from the compound of the formula (2) or (4) and methanol, ethanol, butanol, propylene glycol or hexanol was orally administered to a SD rat as a test sample for 4 weeks continually at a dose of 4 mg/kg/day.

General physical condition of the rats was observed and the weights were measured during the oral administration, and pathologic autopsy was performed after the administration. Consequently, abnormal results were not observed compared to control.

Administration tests for humans using the polyester cyclic compound of the formula (2) will be shown below in the following examples 43 to 66 and explained in detail.

Example 43

The compound of Example 3 was administered (oral administration) to a patient (10 years: male) with brain tumor at a dose of 100 mg/day. Consequently, visual problems and speech disorder, which the patient had been suffering from, were improved in about one week and the reduction of the tumor was observed.

Example 44

The compound of Example 2 was administered (oral administration) to a patient (73 years: male) suffering from prostatic malignant tumor at a dose of 60 mg/day. Consequently, subjective symptoms were improved in a few days and the reduction of the tumors was confirmed, thereby eliminating the need for surgical operation, in about two weeks.

Example 45

The compound of Example 4 was administered (oral administration) to a patient (48 years: male) suffering from prostatic hypertrophy at a dose of 60 mg/day. Consequently, symptoms such as bleeding, difficulty of urination and residual urine were improved in two or three days.

Example 46

The compound of Example 4 was administered (oral administration) to a patient (84 years: female) suffering from rheumatism at a dose of 60 mg/day. Consequently, symptoms such as pain and swelling, which had not been improved by the other medication, were improved in about 1 month and blood test showed that rheumatoid markers were decreased.

Example 47

The compound of Example 4 was administered (oral administration) to a patient (64 years: male) suffering from diabetes at a dose of 200 mg/day. Consequently, subjective symptoms such as trembling of fingers were improved and his blood sugar and glycosuria were decreased in about 1 month.

Example 48

The compound of Example 2 was administered (oral administration) to a patient (60 years: female) suffering from breast cancer at a dose of 100 mg/day. Consequently, her physical condition was recovered and the reduction of the cancer metastasized to the liver was confirmed in about 1 month. The administration was further continued and the cancer was almost disappeared in about 2 months.

Example 49

The compound of Example 3 was administered (oral administration) to a patient (46 years: male) suffering from gastric cancer at a dose of 100 mg/day. Consequently, his physical condition was recovered in about 1 month and metastatic focus was disappeared in about 2 months. Primary focus was also cured.

Example 50

The compound of Example 3 was administered (oral administration) to a patient (66 years: male) suffering from lung cancer at a dose of 100 mg/day. Consequently, the reduction of the focus was confirmed in about 2 months.

Example 51

The compound of Example 3 was administered (oral administration) to a patient (40 years: male) suffering from pharyngeal cancer at a dose of 100 mg/day. Consequently, his physical condition was improved and the number of leukocytes was recovered to a normal value in about 1 month. Thereafter, the reduction of the cancer and the falling-out of the tumor tissue from pharynx were observed.

Example 52

The compound of Example 4 was administered (oral administration) to a patient (32 years: female) suffering from allergic rhinitis and pollen allergy at a dose of 20 mg/day. Consequently, these symptoms were disappeared which had been relieved but not disappeared by administering commercial drugs.

Example 53

The compound of Example 4 was administered (oral administration) to a patient (44 years: male) suffering from hepatic insufficiency at a dose of 60 mg/day. Consequently, values of blood test were recovered to normal values, his physical condition was improved and the other measured values were also improved in about two weeks.

Example 54

The compound of Example 4 was administered (oral administration) to a patient (53 years: female) suffering from parkinson disease at a dose of 100 mg/day. Consequently, her physical condition, exercise function and muscular strength were improved, so that she became able to live daily life without particular difficulties.

Example 55

The compound of Example 4 was administered (oral administration) to a patient (45 years: female) suffering from collagen disease at a dose of 100 mg/day. Consequently, her ache or pain was disappeared in two or three days and administration of an analgesic obtained from a doctor was stopped.

Example 56

The compound of Example 4 was administered (oral administration) to a patient (46 years: male) suffering from bronchial asthma at a dose of 60 mg/day. Consequently, cough and phlegm were decreased to eliminate the need for a medicine of inhalation.

Example 57

The compound of Example 4 was administered (oral administration) to a patient (40 years: female) suffering from Meniere syndrome at a dose of 100 mg/day. Consequently, her subjective symptoms were relieved in two or three days. After continuing the administration, the symptoms of the syndrome were disappeared.

Example 58

The compound of Example 4 was administered (oral administration) to a patient (58 years: female) suffering from hypertension at a dose of 30 mg/day. Consequently, the blood pressure was decreased to a value near normal values in about 1 month.

Example 59

The compound of Example 4 was administered (oral administration) to a patient (50 years: female) having shoulder tension and a cold constitution at a dose of 30 mg/day. Consequently, each symptom was clearly improved in about two weeks, eliminating the need for instruments such as warm keeper which had been used.

Example 60

The compound of Example 4 was administered (oral administration) to a patient (40 years: male) suffering from chronic fatigue at a dose of 30 mg/day. Consequently, he became free from the fatigue and hangover after drinking in about one week.

Example 61

The compound of Example 4 was administered (oral administration) to a patient (34 years: female) suffering from constipation at a dose of 30 mg/day. Consequently, her bowel movement was activated and evacuation was normalized in about 1 or 2 days.

Example 62

The compound of Example 4 was administered (oral administration) to a patient (14 years: male) having a lot of pimples at a dose of 30 mg/day. Consequently, his skin became smoother in about two weeks.

Example 63

The compound of Example 4 was administered (oral administration) to a patient (34 years: female) suffering from severe menstrual pain at a dose of 30 mg/day. Consequently, low back pain and nausea caused by the menstrual pain were relieved which had not been improved by commercial drugs, and the symptoms were improved, so that she became able to live daily life without particular difficulties.

Example 64

A patient (60 years: female) suffering from skin cracks and chaps applied, onto the affected parts, solution of 60 mg of the compound of Example 4 dissolved into 5–6 ml of water. Consequently, the above symptoms were improved in 1 to 3 days.

Example 65

A patient (5 years: female) suffering from severe atopic dermatitis applied, onto the affected parts, commercial ointment containing the compound of Example 4 in a concentration of 5%. Consequently, the symptoms were improved in about 1–2 weeks.

Example 66

A patient (34 years: female) suffering from severe corns with pain applied, onto the affected parts, commercial hand cream containing the compound of Example 4 in a concentration of 5%. Consequently, the pain was relieved in 1–2 days and the symptoms were improved in 2–3 weeks.

Industrial Applicability

As described above, the polyester cyclic compound and the complex of the polyester cyclic compound of the invention demonstrate many pharmacological effects such as carcinostatic effect and immunological regulation specifically to a living body. Moreover, by the effect of the OH group-containing compound, the polyester cyclic compound may be easily absorbed into a living body so that the pharmacological effects are further improved. Moreover, the polyester cyclic compound hardly demonstrates any toxicity. Therefore, by administering the cyclic compound or the complex to human, the compound and the complex is particularly effective to medication or prevention of cancer, rheumatism, prostic disease, dementia, chronic hepatitis, autoimmune disease, allergic disease, menopausal syndrome, menstrual pain or adult diseases such as diabetes and hypertension. The compound or the complex is also effective to medication or prevention of diseases of animals.

Moreover, the polyester cyclic compound has properties to form a complex with an OH group-containing compound and to form a bonded body with a compound having ester groups such as a phosphoric group or sulfuric group or the like. Therefore, the polyester cyclic compound may be reacted with a drug having an OH group or a ester group and thereby development of a novel drug and novel reagent is expected. Moreover, the compound, the complex or the bonded body is expected to be used as a catalyst during a synthetic reaction process.

What is claimed is:

1. A cyclic polyester compound of the formula

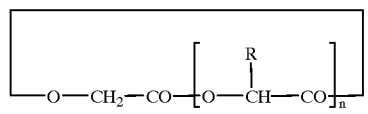
(1)

where each R is a $C_{1-5}$ alkyl group or a $C_{1-5}$ alkyl group in which at least a hydrogen atom is replaced with a fluorine atom, and n is an integer of 2 to 9.

2. The compound of claim 1 wherein R is a $C_{1-3}$ alkyl group or fluorinated $C_{1-3}$ alkyl group.

3. The compound of claim 1 wherein R is methyl.

4. The compound of claim 1 of the formula:

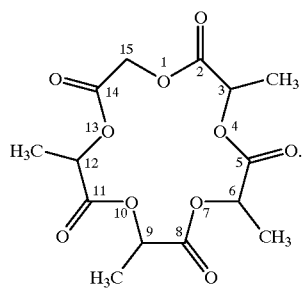
(6)

5. The compound of claim 1 of the formula:

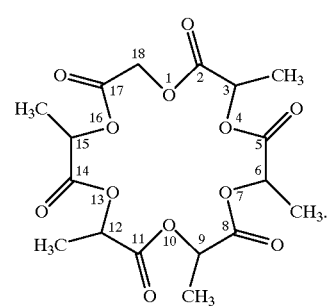
(7)

6. A cyclic polyester compound of the formula

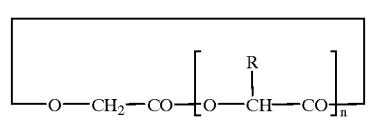
(1)

where each R is a hydrogen atom, $C_{1-5}$ alkyl group or a $C_{1-5}$ alkyl group in which at least a hydrogen atom is replaced with a fluorine atom, and n is an integer of 2 to 9, provided that when R is hydrogen n is 1–3 or 6–9.

7. A complex of at least one compound containing an OH group and at least one polyester cyclic compound selected from the group consisting of:

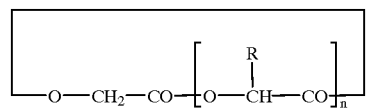
(1)

where each R is a hydrogen atom, a $C_{1-5}$ alkyl group or a $C_{1-5}$ alkyl group in which at least a hydrogen atom is replaced with a fluorine atom, and n is an integer of 2 to 9;

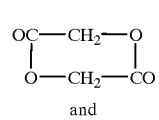
(3)

and

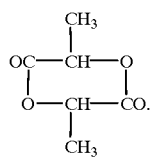
(4)

8. The complex as claimed in claim 7, wherein the compound containing an OH group or groups is selected from a group consisting of an organic compound having an alcoholic hydroxyl group, a phenolic hydroxyl group and a hydroxy acid.

9. A bonded body comprising at least one ester compound and a complex of at least one compound containing an OH group and at least one polyester cyclic compound selected from the group consisting of

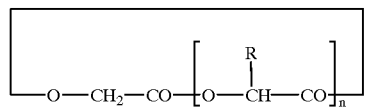
(1)

where each R is a hydrogen atom, a $C_{1-5}$ alkyl group or a $C_{1-5}$ alkyl group in which at least a hydrogen atom is replaced with a fluorine atom, and n is an integer of 2 to 9;

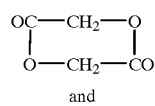
(3)

and

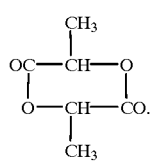
(4)

10. A bonded body comprising at least one ester compound and at least one polycyclic compound selected from formulas (1), (3) and (4)

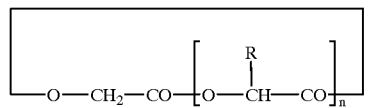
(1)

where each R is a hydrogen atom, a $C_{1-5}$ alkyl group or a $C_{1-5}$ alkyl group in which at least a hydrogen atom is replaced with a fluorine atom, and n is an integer of 2 to 9;

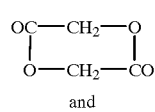
(3)

and

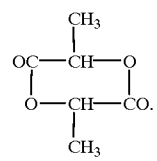
(4)

11. A composition comprising together with a carrier or diluent a cyclic polyester compound of the formula

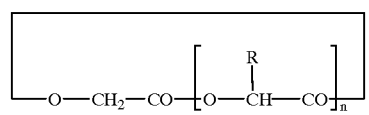
(1)

where each R is a hydrogen atom, $C_{1-5}$ alkyl group or a $C_{1-5}$ alkyl group in which at least a hydrogen atom is replaced with a fluorine atom, and n is an integer of 2 to 9.

12. A composition comprising together with a carrier or diluent the compound of claim 6, 7, 9 or 10.

13. An orally administrable composition comprising together with a carrier or diluent a cyclic polyester compound of the formula

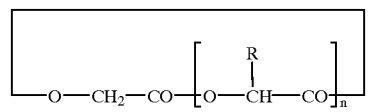
(1)

where each R is a hydrogen atom, $C_{1-5}$ alkyl group or a $C_{1-5}$ alkyl group in which at least a hydrogen atom is replaced with a fluorine atom, and n is an integer of 2 to 9.

14. An orally administrable composition comprising together with a carrier or diluent the compound of claim 6, 7, 9 or 10.

15. A method of treating a condition selected from the group consisting of cancer. rheumatism, prostic disease, dementia, chronic hepatitis, autoimmune disease, allergic disease, menopausal syndrome, menstrual pain, diabetes and hypertension, said method comprising administering an effective amount of a cyclic polyester compound of the formula

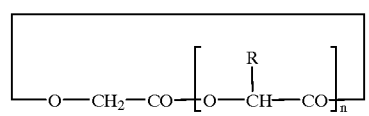
(1)

where each R is a hydrogen atom, $C_{1-5}$ alkyl group or a $C_{1-5}$ alkyl group in which at least a hydrogen atom is replaced with a fluorine atom, and n is an integer of 2 to 9.

16. A method of treating a condition selected from the group consisting of cancer, rheumatism, prostic disease, dementia, chronic hepatitis, autoimmune disease, allergic disease, menopausal syndrome, menstrual pain, diabetes and hypertension, said method comprising administering an effective amount of the compound of claim 6, 8, 9 or 10.

17. A method of providing immunological regulation comprising administering an effective amount of a cyclic polyester compound of the formula

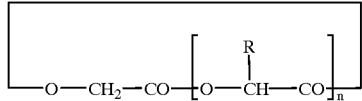
(1)

where each R is a hydrogen atom, $C_{1-5}$ alkyl group or a $C_{1-5}$ alkyl group in which at least a hydrogen atom is replaced with a fluorine atom, and n is an integer of 2 to 9.

18. A method of providing immunological regulation comprising administering an effective amount of the compound of claim 6, 8, 9 or 10.

* * * * *